United States Patent [19]

Lipton et al.

[11] 4,348,205

[45] Sep. 7, 1982

[54] MEASURING BETA-HYDROXYBUTYRATE CONCENTRATION IN URINE

[76] Inventors: Stuart A. Lipton, 125 Pleasant St., Apt. #601, Brookline, Mass. 02146; James V. Manzione, Jr., 38 Meadow La., Glen Head, N.Y. 11545

[21] Appl. No.: 188,749

[22] Filed: Sep. 19, 1980

[51] Int. Cl.$^3$ .............................................. G01N 33/64
[52] U.S. Cl. ..................................... 23/230 B; 23/930
[58] Field of Search ............... 23/230 B, 930; 252/408

[56] References Cited

U.S. PATENT DOCUMENTS 4,147,514  4/1979  Magers et al. ..................... 23/230 B

OTHER PUBLICATIONS

Bauer et al., "Clinical Laboratory Methods", The C. V. Mosby Co., Saint Louis, 1974, p. 39.
Black, Journal of Biological Chemistry, vol. 5, 207–210, 1908–1909.
Dakin, Journal of Biological Chemistry, vol. 4, 91–100, 1908.
Shaffer, Journal of Biological Chemistry, vol. 5, 211–223, 1908–1909.

*Primary Examiner*—Arnold Turk
*Attorney, Agent, or Firm*—W. R. Hulbert

[57] ABSTRACT

A method of measuring the beta-hydroxybutyrate concentration of a urine sample including, in one step, the oxidation of beta-hydroxybutyrate to acetone and acetoacetate and the removal of pre-existing acetone/acetoacetate.

4 Claims, No Drawings

MEASURING BETA-HYDROXYBUTYRATE CONCENTRATION IN URINE

BACKGROUND OF THE INVENTION

This invention relates to the measurement of beta-hydroxybutyrate in urine.

Accurate measurements of beta-hydroxybutyrate concentration are invaluable in diagnosing certain types of acidoses, e.g., alcoholic acidoses, and acidoses induced by starvation, asphyxia, ketosis, or hyperosmolar, hyperglycemic, non-ketotic coma.

The Hart test, described in *Clinical Laboratory Methods* Bauer, Ackermann, and Toro, editors (C. V. Mosby Co., St. Louis, 1974) is used to measure beta-hydroxybutyrate and involves adding equal volumes of dilute acetic acid and water to a 20 ml urine sample. The acidified urine is boiled to half its volume to remove acetone/acetoacetate, and is then cooled. Next, hydrogen peroxide and additional water are added, and the solution is warmed and cooled again. This second heating converts the beta-hydroxybutyrate to acetone and acetoacetate, whose presence is detected colorimetrically by adding nitroprusside solution, acetic acid, and ammonia.

SUMMARY OF THE INVENTION

My invention provides a simple, rapid method for the measurement of the beta-hydroxybutyrate concentration in a very small urine sample. By the simultaneous use of hydrogen peroxide and of heat of about 100°0 C., the steps of vaporizing the pre-existing acetone/acetoacetate and of converting beta-hydroxybutyrate to acetone/acetoacetate can be performed in a single operation without the addition of acid. Acetone/acetoacetate is released after 8–13 minutes of heating, and beta-hydroxybutyrate is oxidized in 20–30 minutes, so that, after 20 to 28 minutes of heating, all of the originally-present acetone/acetoacetate (which would interfere with the test) has been eliminated, and all of the beta-hydroxybutyrate has been oxidized but not vaporized (as it would be if heating continued).

The method of the invention detects beta-hydroxybutyrate concentrations as low as 5 mM, and gives graded measurements over the range 5–35 mM, within which range have occured clinical beta-hydroxybutyrate levels associated with various acidoses.

DESCRIPTION OF THE PREFERRED EMBODIMENT

One drop of 30% hydrogen peroxide was added to a test tube containing ten drops of a urine sample. The test tube was then placed in a gently boiling water bath for 28 minutes. Any pre-existing acetone/acetoacetate was released as volatile acetone and carbon dioxide after approximately 13 minutes, and after 28 minutes any beta-hydroxybutyrate was oxidized to acetone and acetoacetate.

The test tube was then cooled, and acetone/acetoacetate measured using the nitroprusside test. This gave an accurate measure of beta-hydroxybutyrate originally present in the sample.

What is claimed is:

1. A process of measuring beta-hydroxybutyrate in a urine sample consisting essentially of
   providing said urine sample free of any additions of acid solutions,
   mixing hydrogen peroxide with said urine sample,
   heating said urine and hydrogen peroxide mixture at a temperature of about 100° C. for a period of time sufficient to vaporize all of any acetone/acetoacetate originally present in said sample and to oxidize beta-hydroxybutyrate in said sample to acetone/acetoacetate,
   cooling said mixture, and
   measuring the acetone/acetoacetate concentration using the nitroprusside test, said concentration being a measure of said beta-hydroxybutyrate originally present in said urine sample.

2. The process of claim 1 wherein said hydrogen peroxide and said urine sample are mixed in the volumetric proportion of about one part 30% hydrogen peroxide solution to ten parts urine sample.

3. The process of claim 1 wherein said period of time is 20–28 minutes.

4. The process of claim 3 wherein said period of time is about 28 minutes.

* * * * *